US00PP29984P2

(12) United States Plant Patent
Carruth

(10) Patent No.: US PP29,984 P2
(45) Date of Patent: Dec. 18, 2018

(54) SHRUB ROSE PLANT NAMED 'WEKSWECHEFY'

(50) Latin Name: *Rosa hybrida*
Varietal Denomination: WEKswechefy

(71) Applicant: Early Morning LLC, Lawrenceburg, IN (US)

(72) Inventor: Thomas F. Carruth, Altadena, CA (US)

(73) Assignee: Early Morning LLC, Pomona, CA (US)

( * ) Notice: Subject to any disclaimer, the term of this patent is extended or adjusted under 35 U.S.C. 154(b) by 0 days.

(21) Appl. No.: 15/732,591

(22) Filed: Nov. 30, 2017

(51) Int. Cl.
*A01H 5/02* (2018.01)

(52) U.S. Cl.
USPC ..... Plt./102

(58) Field of Classification Search
USPC ..... Plt./102
See application file for complete search history.

(56) References Cited

U.S. PATENT DOCUMENTS

PP5,975 P 5/1987 Moore

*Primary Examiner* — Annette H Para
(74) *Attorney, Agent, or Firm* — McKee, Voorhees & Sease, PLC

(57) ABSTRACT

A new variety of Shrub rose suitable for garden decoration, having flowers of lavender pink with purple magenta eye coloration.

1 Drawing Sheet

Classification: The present invention relates to a new *Rosa hybrida* plant.

Variety denomination: The new plant has the varietal denomination 'WEKswechefy'.

BACKGROUND OF THE INVENTION

This invention relates to a new and distinct variety of Shrub Rose. It has as its seed parent the variety known as 'MORchari' (U.S. Plant Pat. No. 5,975) and as its pollen parent the variety known as 'PEJbigeye' (not patented).

SUMMARY OF THE INVENTION

Among the features which distinguish the new variety from other presently available and commercial rose cultivars known to the inventor are the following combinations of characteristics: its unusual lavender pink with purple magenta eye flower coloration, its lanceolate shaped terminal leaflets and its many stipitate glands on the underside of the young leaves and on the new shoots, rachis, petiole and underside of the stipule of the young leaves. The plant has a bushy rounded moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKswechefy' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'MORchari' by the following combination of characteristics: whereas 'WEKswechefy' bears semi-double flowers (about 11 to 18 petals) of lavender pink with purple magenta eye coloration, 'MORchari' bears very double flowers of lavender to pink lavender coloration with significantly heavier petalage (about 55 to 60 petals). The new variety has a bushy rounded moderately spreading medium height growing habit (about 105 to about 145 cm. in height), whereas the seed parent has a dwarf bushy spreading significantly shorter growing habit (about 26 to about 30 cm. in height).

The new variety may be distinguished from its pollen parent, 'PEJbigeye' by the following combination of characteristics: whereas 'WEKswechefy' bears small sized flowers (about 5.0 to about 6.8 cm. in diameter) produced in large clusters of up to thirty-six or more per stem, 'PEJbigeye' bears significantly larger flowers (about 10.5 cm. in diameter) produced in significantly smaller clusters of about 2 to 5 flowers per stem.

COMPARISON WITH THE CLOSEST COMMERCIALLY AVAILABLE CULTIVAR

The closest commercially available cultivar to the new variety is the pollen parent 'PEJbigeye' (not patented).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November. Throughout this specification, color references and/or values are based upon the Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers in clusters of two to thirty-six or more per stem. Flowers are borne in regular rounded to somewhat pyramidal clusters on strong short to long stems (about 15 to about 100 cm.). The cluster ranges from about 5.2 to about 12.8 cm. in diameter. Outdoors, the plant blooms abundantly and nearly continuously during the growing season. The flowers have a strong citrus-like to fruity and spices fragrance.

BUD

The peduncle is about 1.5 to about 3.2 cm. in length, of slender caliper (about 0.15 to about 0.2 cm. in diameter), and usually erect. It is moderately smooth, with some stipitate glands, and very few hairs. Peduncle color is between 146D and 146A sometimes lightly suffused, especially on the side exposed to the sun, with between 187B and 187C.

Before the calyx breaks, the bud is about 0.7 to about 1.0 cm. in diameter at the widest point, about 0.8 to about 1.3 cm. in length, and pointed to somewhat ovoid in shape. The surface of the bud bears between 5 to 7 foliaceous appendages with some stipitate glands, usually with slender entire foliaceous parts extending beyond the tip of the bud about ½ or more of its length. Bud color is between 146C and 146A often moderately suffused, especially on the side exposed to the sun, with between 187B and 187A.

The sepals are 5 per flower, about 1.2 to about 1.7 cm. in length and about 0.4 to about 0.6 cm. in width at the widest point. The outer surface color of the sepal is between 146C and 146A often moderately suffused, especially on the side exposed to the sun, with between 187B and 187A. The outer surface of the sepal is somewhat rough and bears between 0 to 4 foliaceous appendages with some stipitate glands. The inner surface color of the sepal is near 146C broadly bordered by near 137B. After the sepals open, the inner surface color is often heavily suffused, especially on the area exposed to the sun, with between 187A and 187B. The inner surface of the sepal is covered with fine wooly tomentum; sepal margins are entire and lined with some stipitate glands and numerous hairs. The sepals are moderately permanent, and usually straight in shape with acute apices.

The receptacle of the flower is of somewhat long length (about 0.4 to about 0.6 cm.) and moderately thin in caliper (about 0.5 to about 0.7 cm. in diameter). The receptacle is urn-shaped in form. Its surface is smooth with somewhat thin fleshy walls. The receptacle color is between 146C and 146A sometimes lightly suffused, especially on the side exposed to the sun, with between 187B and 187C.

As the petals open (after the calyx breaks), the bud is about 0.8 to about 1.4 cm. in diameter at the widest point, about 1.1 to about 1.6 cm. in length, and moderately ovoid to somewhat pointed in form. The color of the under surfaces of the newly opened petals is between 20B and 11B sometimes moderately suffused with between 61B and 61C. There is no visible change in coloration at the point where the petal attaches. The color of the upper surfaces of the newly opened petals is between 58B and 53D. At the point where the petal attaches, there is a very small zone of between 4A and 5C. The attachment zone is surrounded by an eye zone of about 0.7 to 0.8 cm in diameter. The eye zone color is between 187A and 53A.

BLOOM

When fully open, the bloom ranges from about 5.0 to about 6.8 cm. in diameter. Petalage is semi-double with about 11 to 18 petals and about 1 to 5 petaloids irregularly arranged. When partially open, the bloom form is moderately cupped to somewhat high centered, and the petals are loosely spiraled to cupped to somewhat undulated with petal edges moderately reflexed inward. When fully open, the bloom form is more cupped to somewhat flat, and the petals are loosely cupped to somewhat undulated with petal edges sometimes moderately reflexed inward to usually moderately reflexed outward to somewhat rolled outward.

PETALS

The substance of the petals is moderately heavy and of medium to somewhat thick thickness, with upper surfaces moderately satiny to somewhat velvety and under surfaces slightly shiny. The petals are about 2.4 to about 3.1 cm. in length and about 1.4 to about 3.0 cm. in width at the widest point. Petal margins are entire.

The outer petals are moderately obovate to somewhat rounded in shape with rounded apices.

The inner petals are broadly obovate in shape with rounded apices and sometimes slightly notched with one notch.

Petaloids are about 0.8 to about 2.6 cm. in length and about 0.3 to about 2.1 cm. in width at the widest point. Petaloids are irregularly shaped somewhat oblanceolate to subulate with rounded apices.

NEWLY OPENED FLOWER

The under surface color of the outer, intermediate and inner petals is between 20D and 155C sometimes lightly suffused with between 61B and 61C. There is no visible change in coloration at the point where the petal attaches. The upper surface color of the outer, intermediate and inner petals is between 74D and 78D. At the point where the petal attaches, there is a very small zone of near 15C. The attachment zone is surrounded by an eye zone of about 1.1 to 1.5 cm in diameter. The eye zone color is between 79A and 71A to as dark as near 187A with a thin circular band of between 74B and 71B.

The under and upper surface colors of the petaloids are similar in coloration to the upper and under surfaces of the intermediate and inner petals.

The general tonality of the newly opened flower is between 74D and 78D with a large eye zone at the base of the petal of between 79A and 71A to as dark as near 187A with a thin circular band of between 74B and 71B.

THREE-DAY-OLD FLOWER

The under surface color of the outer, intermediate and inner petals is between 69D and 155C. There is no visible change in coloration at the point where the petal attaches. The upper surface color of the outer, intermediate and inner petals is between 75C and 75B. At the point where the petal attaches, there is a very small zone of between 11C and 13D. The attachment zone is surrounded by an eye zone of about 1.1 to 1.5 cm in diameter. The eye zone color is between 79A and 79B with a thin circular band of between 78A and 72B.

The under and upper surface colors of the petaloids are similar in coloration to the upper and under surfaces of the intermediate and inner petals.

The general tonality of the three-day-old flower is between 75C and 75B with a large eye zone at the base of the petal of between 79A and 79B with a thin circular band of between 78A and 72B.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids. The filaments are of short to long length (about 0.3 to about 0.9 cm.) most with anthers. Filaments are between 13C and 12B in color with between 187B and 187C at the base. The anthers are of somewhat small to medium size for the class and all open approximately at the same time. Anther color when immature is near 16B on the external part and near 13D on the internal part. Anther color at maturity is near 164A on the external part and near 200A on the internal part. Pollen is moderate and between 18B and 16D in color.

FEMALE REPRODUCTIVE ORGANS

Pistils vary in number (average about 45). The styles are moderately even, average in length (about 0.4 to about 0.6 cm.), somewhat thin in caliper, and loosely bunched. Stigma color is near 16C. Style color is between 4D and 2D often moderately suffused near the top with between 53B and 53C. Ovaries are usually all enclosed in the calyx. The ovaries are of small size and between 157B and 157A in color.

Hips have not been observed on this variety when grown in Pomona, Calif.

FOLIAGE

The compound leaves are usually comprised of three to seven leaflets and are borne abundantly. The seven-leaflet leaves are about 9.0 to about 14.8 cm. in length and about 5.0 to about 11.0 cm. in width at the widest point, moderately crisp to somewhat leathery in texture on both sides, and glossy in finish on the upper side and matte in finish on the underside. The leaves have a pinnate venation pattern. The terminal leaflets are about 2.8 to about 5.7 cm. in length and about 1.4 to about 2.6 cm. in width at the widest point, shaped lanceolate with acute apices and rounded bases. Their margins are usually simply serrate.

The upper surface color of the mature leaf is between 139A and 137A. The under surface color of the mature leaf is between 147B and 137A. The under and upper colors of the leaf veins on the mature leaf are similar in coloration to the upper and under surfaces colors of the mature leaf. The upper surface color of the young leaf is between 137C and 137A, sometimes lightly suffused with between 187A and 187B. The under surface color of the young leaf is between 138B and 137A, sometimes lightly suffused with between 187B and 187A. The under and upper colors of the leaf veins on the young leaf are similar in coloration to the upper and under surfaces colors of the young leaf. The under surface of the young leaf bears many stipitate glands.

The rachis is about 4.8 to about 7.4 cm. in length, about 0.1 to about 0.15 cm in width at the widest point, and rough. The upper side is deeply grooved with many hairs and some stipitate glands on the edges of the grooves. The under side of the rachis is rough with some stipitate glands and few small prickles. There are many stipitate glands on both sides of the rachis on the young leaf. The rachis color is near 146D on the under side and near 137B on the upper side, sometimes lightly suffused on the young leaves with between 187B and 187C.

The stipules are about 1.0 to about 1.8 cm. in length and of medium width (about 0.4 to about 0.7 cm.) with long straight points that usually turn out at an angle of more than 45 degrees and sometimes recurve toward the stem. There are many stipitate glands on the underside of the stipules on the young leaf. The under and upper surface color of the stipule is between 137A and 137B. The upper and under surfaces of the stipules are smooth in texture.

The petiole is somewhat light in caliper and rough. The upper side is deeply grooved with many hairs and some stipitate glands on the edges of the grooves. The under side of the petiole is rough with some stipitate glands and few small prickles. There are many stipitate glands on both sides of the petiole on the young leaf. The petiole is about 0.7 to about 1.2 cm. in length and about 0.1 to about 0.15 cm in width at the widest point. The petiole color is near 146D on the underside and near 137B on the upper side, sometimes lightly suffused on the young leaves with between 187B and 187C.

The plant displays an above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Pomona, Calif. The plant's winter hardiness and drought/heat tolerance are yet to be determined.

GROWTH

The plant has a bushy rounded moderately spreading medium height growing habit (about 105 to about 145 cm. in height and about 110 to about 120 cm. spread at the widest point), with very full branching. It displays vigorous growth and the canes are of somewhat light to medium caliper for the class (about 0.9 to about 1.4 cm. in diameter at the widest point).

The color of the major stems is near 199A. The major stems are rough in texture and they bear some large prickles that are about 0.7 to about 1.2 cm. in length. The large prickles are angled slightly downward with a moderately short narrow oval base; prickle color is between 200B and 165A often moderately suffused with between 201B and 201C. The major stem bears several small prickles of similar shape and coloration.

The color of the branches is between 146B and 147A. The branches are rough in texture and they bear some large prickles which are of similar size and shape to the large prickles on the major stems; prickle color is near 199A sometimes lightly suffused with between 187B and 187C. The branches bear several small prickles of similar shape and coloration.

The color of the new shoots is between 146C and 147A sometimes lightly suffused with between 187B and 187C. The new shoots are rough in texture and they bear few large prickles which are of similar shape to the large prickles on the major stems. The prickles are about 0.4 to about 0.5 cm. in length. Prickle color is between 152D and 153A often lightly suffused with between 187C and 187D. The shoots bear many small prickles of similar shape and coloration. There are many stipitate glands on the new shoots.

I claim:

1. A new and distinct Shrub rose plant of the variety substantially as described and illustrated herein.

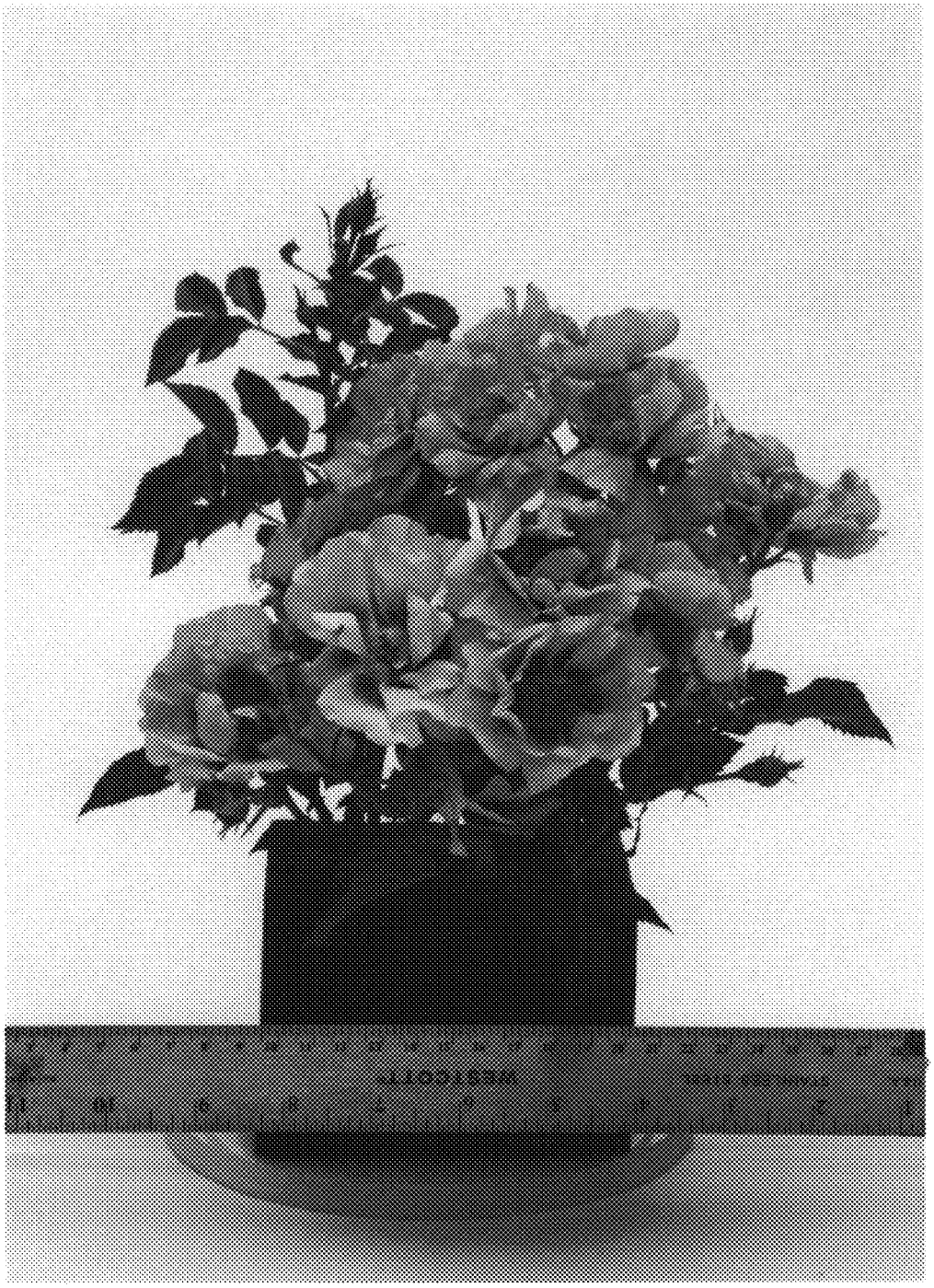

* * * * *